United States Patent [19]

Furuya et al.

[11] Patent Number: 5,153,124
[45] Date of Patent: Oct. 6, 1992

[54] HYDROXYL-ML-236B DERIVATIVES, THEIR PREPARATION AND USE

[75] Inventors: Kouhei Furuya; Takao Okazaki; Yoshio Tsujita; Seigo Iwado; Kiyoshi Hamano; Masao Kuroda; Jun Yoshikawa; Toshiaki Iwai; Kunio Nakano, all of Tokyo, Japan

[73] Assignee: Sankyo Company Limited, Tokyo, Japan

[21] Appl. No.: 393,001

[22] Filed: Aug. 11, 1989

Related U.S. Application Data

[63] Continuation of Ser. No. 203,649, Jun. 1, 1988, abandoned, which is a continuation of Ser. No. 906,034, Sep. 10, 1986, abandoned.

[30] Foreign Application Priority Data

Sep. 13, 1985 [JP] Japan ................. 60-202614
Oct. 8, 1985 [JP] Japan ................. 60-224153

[51] Int. Cl.⁵ .................. G12P 17/06; G12N 1/20
[52] U.S. Cl. ................... 435/125; 435/252.1; 435/253.5; 544/292; 560/188; 560/119
[58] Field of Search .......... 435/125, 253.5, 252.1; 549/292; 560/188, 119

[56] References Cited

U.S. PATENT DOCUMENTS 4,346,227 0/1982 Terahara et al. ............... 560/119
4,376,838 3/1983 Lam ............................. 549/292

FOREIGN PATENT DOCUMENTS 2075013 11/1981 United Kingdom ............... 549/292

OTHER PUBLICATIONS

Sariaslani, F. S., et al. (1986) Biochem. Biophys. Res. Comm. 141(2), 405–410.
Serizawa et al I, *Chemical Abstracts*, vol. 99, No. 35805n, 1983.
Serizawa et al II, *Chemical Abstracts*, vol. 99, No. 35806p, 1983.
Serizawa et al, Journal of Antibiotics, May 1983, pp. 604–607.
Serizawa et al, Journal of Antibiotics, May 1983, pp. 608–610.

*Primary Examiner*—Charles L. Patterson, Jr.
*Attorney, Agent, or Firm*—Frishauf, Holtz, Goodman & Woodward

[57] ABSTRACT

Derivatives of ML-236B carboxylic acid, its salts and esters and corresponding lactone have a hydroxy group at the 3"-position and optionally also at the 6'-position. These derivatives may be prepared by the enzymatic hydroxylation of a corresponding ML-236B compound employing an enzyme produced by a microorganism of the genus Streptomyces or Amycolata, especially Streptomyces sp. SANK 62285, Streptomyces sp. SANK 62385, Streptomyces sp. SANK 62485, Streptomyces sp. SANK 62585, *Amycolata autotrophica* SANK 62781, *Amycolata autotrophica* subsp. *canberrica* SANK 62882 or *Amycolata autotrophica* subsp. *amethystina* SANK 62981. These derivatives have the ability to inhibit cholesterol biosynthesis.

16 Claims, 5 Drawing Sheets

HYDROXYL-ML-236B DERIVATIVES, THEIR PREPARATION AND USE

This application is a continuation of application Ser. No. 07/203,649, filed Jun. 1, 1988, now abandoned which is a continuation of Ser. No. 06/906,034 filed Sep. 10, 1986 (abandoned).

BACKGROUND TO THE INVENTION

The present invention relates to certain novel hydroxy-ML-236B derivatives, as well as salts and esters of these compounds, and processes for preparing them and methods and compositions using them.

ML-236B, which can exist in the form of an acid (known as "ML-236B carboxylic acid") or a lactone (known as "ML-236B lactone"), was disclosed in United Kingdom Patent Specification No. 1,453,425 and, in its lactone form, has the formula (A):

Subsequently, United Kingdom Patent Specification No. 1,555,831 disclosed a variety of salts and esters of ML-236B. ML-236B and its salts and esters were found to inhibit the biosynthesis of cholesterol by competing with 3-hydroxy-3-methylglutaryl coenzyme A reductase, which is the rate-determining enzyme for cholesterol biosynthesis; these compounds were thus found to exhibit a very marked ability to reduce serum cholesterol levels.

Subsequently, certain 3-hydroxy-ML-236B derivatives were isolated as products of the animal metabolism of ML-236B lactone and similar derivatives were found to be produced by the enzymatic hydroxylation of ML-236B lactone or carboxylic acid or salts or esters thereof, effected by means of various microorganisms. These processes are disclosed in U.S. Pat. No. 4,346,227 and UK Patent No. 2,111,052, and the compounds thus produced are described in those patents as M-4, M-4', IsoM-4 and IsoM-4'. These compounds were found to have an ability to inhibit the biosynthesis of cholesterol which is at least comparable with and, in some instances, substantially exceeds that of ML-236B itself.

ML-236B and its derivatives, including the M-4 and M-4' compounds, are thus of therapeutic value for the treatment of hyperlipaemia and the prophylaxis of arteriosclerosis.

A structurally related group of compounds includes the mevinolin derivatives e.g. of U.S. Pat. No. 4,231,938, and a hydroxy derivative of such a compound is disclosed in U.S. Pat. No. 4,376,863; however, such compounds are structurally and conceptually different from those of the present invention and are prepared in a different way.

We have now discovered a series of novel hydroxy derivatives of ML-236B which likewise have a valuable ability to inhibit the biosynthesis of cholesterol.

BRIEF SUMMARY OF INVENTION

Accordingly, the present invention provides compounds of formula (I):

wherein R represents a hydrogen atom or a hydroxy group, pharmaceutically acceptable salts and esters thereof and the corresponding ring-closed lactones.

The invention also provides a process for preparing the compounds of the invention, which process comprises contacting an ML-236B compound which is ML-236B carboxylic acid, having the formula (II):

a salt or ester thereof or the corresponding ML-236B lactone with a hydroxylation enzyme produced by a microorganism selected from the group consisting of microorganisms of the genus Streptomyces and microorganisms of the genus Amycolata (as a result of a taxonomic review, microorganisms of this application previously considered to be designated in the genus Nocardia are currently placed in the genus Amycolata—International Journal of Systematic Bacteriology (1986), 36, 29); if necessary, subjecting the resulting product to one or more of hydrolysis, salification, esterification and lactonisation; and isolating the product from the reaction mixture.

DETAILED DESCRIPTION OF INVENTION

For the avoidance of doubt, the numbering system employed in relation to the compounds of the present invention is that shown below on the following formula (I):

where R is as defined above.

The compounds of the invention are thus the 3"-hydroxy ML-236B derivatives of formula (III):

and the 3", 6'-dihydroxy ML-236B derivatives of formula (IV):

Preferred compounds of the invention have the same configuration as the parent ML-236B compounds, that is to say as shown in formula (Ia):

where R is as defined above and the wavy line at the 3"-position indicates that the hydroxy group may be in the α- or β-configuration, i.e. in the α-configuration as in formula (Ib):

or the β-configuration as in formula (Ic):

In the case of the 3", 6'-dihydroxy derivatives, the 6'-hydroxy group is preferably in the β-configuration, whilst the 3"-hydroxy group may be in the α- or β-configuration, i.e. as in formula (IVa):

In their ring-closed lactone forms, the compounds of the invention may be represented by the formula (Id):

(Id)

(in which R is as defined above) and, of course, the various configurations indicated by formulae (Ia), (Ib), (Ic) and (IVa) also apply mutatis mutandis to this formula (Id).

The compounds of the present invention can be prepared from the parent ML-236B compounds (i.e. ML-236B carboxylic acid or a salt, ester or lactone thereof) by hydroxylation with a hydroxylation enzyme produced by a microorganism of the genus Streptomyces or of the genus Nocardia. The hydroxylation enzyme may be separated from the cells of the microorganism or, and more preferably, the living organism may be employed. It is, of course, a simple matter to determine whether any given strain of a microorganism produces such a hydroxylation enzyme and whether the hydroxylation enzyme is effective to produce the monohydroxy compound or the dihydroxy compound of the present invention, simply by cultivating the organism in the presence of an ML-236B compound and then subjecting the reaction mixture to a suitable analysis technique to detect the presence of the monohydroxy and-/or dihydroxy compound.

To date, we have found that hydroxylation enzymes produced by Amycolata autotrophica SANK 62781, Amycolata autotrophica subsp. canberrica SANK 62882, Amycolata autotrophica subsp. amethystina SANK 62981 and Streptomyces sp. SANK 62585 are effective to produce the dihydroxy compound of the present invention, whilst Streptomyces sp. SANK 62285, Streptomyces sp. SANK 62385 and Streptomyces sp. SANK 62485 are effective to produce the monohydroxy compound.

Of the above, the strains of Amycolata, that is to say Amycolata autotrophica SANK 62781, Amycolata autotrophica subsp. canberrica SANK 62882 and Amycolata autotrophica subsp. amethystina SANK 62981 have been disclosed in UK Patent No. 2,111,052.

These strains of Nocardia are all publicly available from the Fermentation Research Institute, Ibaraki-ken, Japan under the Accession Nos. FERM P-6181, FERM P-6182 and FERM P-6183, respectively.

The four strains of the genus Streptomyces, that is to say Streptomyces sp. SANK 62285, Streptomyces sp. SANK 62385, Streptomyces sp. SANK 62485 and Streptomyces sp. SANK 62585 are all newly isolated microorganisms and their morphological and physiological properties are given below.

The morphological and physiological properties of the newly isolated microorganisms were determined using conventional media and the methods described by Shirling and Gottlieb [International Journal of Systematic Bacteriology 16, 313-340 (1966)], together with several supplementary tests. Observations of the culture were made after incubation at 28° C. for 14 days. The color names used were assigned according to the "Guide to Color Standard" (a manual published by Nippon Shikisai Kenkyusho, Tokyo, Japan). The characteristics of the cultures were compared with those of various known species of actinomycetes described according to the ISP (International Streptomyces Project) standards and in "The Actinomycetes, Volume 2" by Waksman, "The ISP Report" by Shirling and Gottlieb, "Bergey's Manual of Determinative Bacteriology", 8th edition and other recent literature concerning the taxonomy of the actinomycetes.

1. Morphological Properties

When observed under a microscope and under an electron microscope, the vegetative hyphae of strains SANK 62285, SANK 62385, SANK 62485 and SANK 62585 were all fully developed with branching, and the aerial hyphae were monopodially branched.

The spore chain of strain SANK 62285 is morphologically straight, the spores are spherical to ovoid and their surfaces are smooth. The spore chains of strains SANK 62385 and SANK 62485 are morphologically spiral, the spores are spherical to elliptical and their surfaces are smooth. The spore chain of strain SANK 62585 is usually straight or flexuous, but sometimes spiral and the spore surfaces are smooth. No special organs, such as whirls, sclerotia, basal hyphae fragmentation and sporangia, can be observed on any of strains SANK 62285, SANK 62385, SANK 62485 or SANK 62585.

2. Growth on Taxanomic Media

The growth of the strains on various media are shown in Tables 1-4.

In these Tables, the following abbreviations are used:
G: growth
AM: aerial mycelium
R: reverse
SP: soluble pigment.

TABLE 1

| Media | Item | Property of Strain SANK 62285 |
|---|---|---|
| Sucrose | G | Not so good, yellowish grey (1-9-10) |
| nitrate | AM | Good, powdery, yellowish grey to |
| agar | | bright brownish grey [(1-9-10) to |
| | | (1-7-10)] |
| | R | Bright brownish grey (1-7-10) |
| | SP | None |
| Glucose/ | G | Good, yellowish grey (1-9-10) |
| asparagine | AM | Fair, greyish white (N-9) |
| agar | R | Yellowish grey (1-9-10) |
| | SP | None |
| Glycerin/ | G | Not so good, pale pink (2-8-4) |
| asparagine | AM | Fair, greyish white (N-9) |
| agar | R | Pale pink (2-8-4) |
| (ISP 5) | SP | Pale orange (3-9-4) |
| Starch/ | G | Good, greyish brown (4-6-6) |
| inorganic | AM | Abundant, powdery, bright brownish |
| salt agar | | grey (2-7-10) |
| (ISP 4) | R | Brown (3-4-6) |
| | SP | Pale reddish brown (3-7-4) |
| Tyrosine | G | Good, brown (6-5-6) |
| agar | AM | Good, powdery, bright brownish grey |
| (ISP 7) | | (1-8-10) |
| | R | Brownish black (1-1-6) |
| | SP | Brown (6-5-6) |
| Peptone | G | Good, pale yellowish brown (4-8-9) |
| yeast-iron | AM | None |
| agar | R | Pale yellowish brown (4-8-9) |
| (ISP 6) | SP | None |
| Nutrient | G | Very good, pale yellow (3-9-10) |
| agar | AM | Fair, greyish white (N-9) |
| (Difco) | R | Pale yellow (3-9-10) |
| | SP | None |

TABLE 1-continued

| Media | Item | Property of Strain SANK 62285 |
|---|---|---|
| Yeast-malt agar (ISP 2) | G | Very good, yellowish brown (4-5-8) |
|  | AM | Abundant, powdery, bright brownish grey (1-7-10) |
|  | R | Brownish black (1-1-6) |
|  | SP | Brown (6-4-6) |
| Oatmeal agar (ISP 3) | G | Good, dark yellowish brown (3-4-8) |
|  | AM | Abundant, powdery, brownish grey (2-6-9) |
|  | R | Dark yellowish brown (2-3-7) |
|  | SP | Greyish brown (4-6-6) |
| Potato/ carrot extract agar | G | Poor, brownish grey (3-5-6) |
|  | AM | Good, powdery, olive-grey (1-6-10) |
|  | R | Dark brown (3-3-6) |
|  | SP | None |

TABLE 2

| Media | Item | Property of Strain SANK 62385 |
|---|---|---|
| Sucrose nitrate agar | G | Not so good, yellowish grey (1-9-10) |
|  | AM | Good, powdery, bright brownish grey (1-7-10) |
|  | R | Yellowish grey (2-8-10) |
|  | SP | None |
| Glucose/ asparagine agar | G | Not so good, yellowish grey (1-9-10) |
|  | AM | Fair, bright brownish grey (1-8-10) |
|  | R | Yellowish grey (1-8-10) |
|  | SP | None |
| Glycerin/ asparagine agar (ISP 5) | G | Good, yellowish grey (1-9-10) |
|  | AM | Fair, powdery, yellowish grey (1-9-10) |
|  | R | Yellowish grey (2-9-10) |
|  | SP | None |
| Starch/ inorganic salt agar (ISP 4) | G | Good, yellowish grey (2-8-10) |
|  | AM | Good, powdery, greyish white to olive-grey [(N-9) to (2-6-11)] |
|  | R | Yellowish grey to greyish olive [(2-8-10) to (3-5-10)] |
|  | SP | None |
| Tyrosine agar (ISP 7) | G | Very good, yellowish brown (10-6-8) |
|  | AM | Fair, pale yellowish orange (2-9-9) |
|  | R | Yellowish brown (10-6-8) |
|  | SP | None |
| Peptone yeast-iron agar (ISP 6) | G | Not so good, pale yellowish brown (6-8-9) |
|  | AM | None |
|  | R | Pale yellowish brown (6-8-9) |
|  | SP | None |
| Nutrient agar (Difco) | G | Not so good, pale yellowish brown (6-8-9) |
|  | AM | None |
|  | R | Pale yellowish brown (6-8-9) |
|  | SP | None |
| Yeast-malt agar (ISP 2) | G | Good, yellowish brown (8-7-9) |
|  | AM | Good, powdery, greyish white to bright brownish grey [(N-8) to (1-7-10)] |
|  | R | Dull yellow to greyish yellow-brown [(10-7-9) to (4-5-9)] |
|  | SP | None |
| Oatmeal agar (ISP 3) | G | Very good, yellowish brown (8-6-8) |
|  | AM | Good, powdery, greyish white to bright brownish grey [(N-8) to (1-7-10)] |
|  | R | Yellowish brown to brown [(6-7-8) to (4-4-6)] |
|  | SP | None |
| Potato/ carrot extract agar | G | Poor, yellowish grey (1-9-10) |
|  | AM | Fair, bright brownish grey (1-7-10) |
|  | R | Yellowish grey (1-9-10) |
|  | SP | None |

TABLE 3

| Media | Item | Property of Strain SANK 62485 |
|---|---|---|
| Sucrose nitrate agar | G | Poor, yellowish grey (1-9-10) |
|  | AM | Fair, greyish white (N-9) |
|  | R | Yellowish grey (1-9-10) |
|  | SP | None |
| Glucose/ asparagine agar | G | Poor, yellowish grey (1-9-10) |
|  | AM | Good, powdery, yellowish grey (1-9-10) |
|  | R | Yellowish grey (1-9-10) |
|  | SP | None |
| Glycerin/ asparagine agar (ISP 5) | G | Not so good, yellowish grey (1-9-10) |
|  | AM | Fair, powdery, greyish white (N-9) |
|  | R | Yellowish grey (1-9-10) |
|  | SP | None |
| Starch/ inorganic salt agar (ISP 4) | G | Good, olive-grey (3-7-10) |
|  | AM | Abundant, powdery, bright brownish grey (1-7-10) |
|  | R | Bright brownish grey (2-7-10) |
|  | SP | None |
| Tyrosine agar (ISP 7) | G | Very good, yellowish brown (10-6-4) |
|  | AM | Good, powdery, bright brownish grey (2-8-7) |
|  | R | Bright brown (8-5-6) |
|  | SP | None |
| Peptone yeast-iron agar (ISP 6) | G | Not so good, pale yellowish brown (6-8-9) |
|  | AM | None |
|  | R | Pale yellowish brown (6-8-9) |
|  | SP | None |
| Nutrient agar (Difco) | G | Not so good, pale yellowish brown (6-8-9) |
|  | AM | None |
|  | R | Pale yellowish brown (6-8-9) |
|  | SP | None |
| Yeast-malt agar (ISP 2) | G | Good, yellowish brown (8-6-9) |
|  | AM | Good, powdery, bright brownish grey (1-8-10) |
|  | R | Yellowish brown (8-6-9) |
|  | SP | None |
| Oatmeal agar (ISP 3) | G | Very good, yellowish brown (8-6-8) |
|  | AM | Good, powdery, bright brownish grey (1-7-10) |
|  | R | Dark brown (4-4-8) |
|  | SP | None |
| Potato/ carrot extract agar | G | Poor, yellowish grey (1-9-10) |
|  | AM | Fair, yellowish grey (1-9-10) |
|  | R | Yellowish grey (1-9-10) |
|  | SP | None |

TABLE 4

| Media | Item | Property of Strain SANK 62585 |
|---|---|---|
| Sucrose nitrate agar | G | Not so good, pale yellowish orange (2-9-9) |
|  | AM | Normal, powdery, greyish white (N-9) |
|  | R | Pale yellowish orange (2-9-9) |
|  | SP | None |
| Glucose/ asparagine agar | G | Not so good, yellowish grey to brownish grey [(2-5-9) to (1-9-10)] |
|  | AM | Trace, greyish white (N-9) |
|  | R | Yellowish grey to brownish grey [(2-5-9) to (1-9-10)] |
|  | SP | None |
| Glycerin/ asparagine agar (ISP 5) | G | Not so good, pale yellowish brown (2-7-9) |
|  | AM | Normal, powdery, greyish white (N-9) |
|  | R | Pale yellowish brown (4-8-9) |
|  | SP | None |
| Starch/ inorganic salt agar (ISP 4) | G | Very good, brownish grey (2-6-9) |
|  | AM | Abundant, powdery, yellowish grey to bright olive-grey [(1-9-10) to (2-8-12)] |
|  | R | Pale brown to brownish grey [(2-8-9) to (2-4-9)] |
|  | SP | None |
| Tyrosine agar (ISP 7) | G | Good, dark yellowish brown (4-4-9) |
|  | AM | Very abundant, powdery, yellowish grey to bright olive-grey [(1-9-10) to (2-8-11)] |
|  | R | Dark brownish grey (2-3-9) |
|  | SP | None |
| Peptone yeast-iron agar | G | Good, yellowish brown (4-6-9) |
|  | AM | None |
|  | R | Yellowish brown (4-6-9) |

TABLE 4-continued

| Media | Item | Property of Strain SANK 62585 |
|---|---|---|
| (ISP 6) | SP | None |
| Nutrient agar (Difco) | G | Not so good, bright olive-grey (4-8-10) |
|  | AM | None |
|  | R | Bright olive-grey (4-8-10) |
|  | SP | None |
| Yeast-malt agar (ISP 2) | G | Very good, yellowish brown (6-7-9) |
|  | AM | Very abundant, powdery, bright olive-grey (2-8-11) |
|  | R | Yellowish brown (6-5-9) |
|  | SP | None |
| Oatmeal agar (ISP 3) | G | Very good, greyish yellow brown (4-5-9) |
|  | AM | Very abundant, powdery, bright olive-grey (2-8-12) |
|  | R | Dark brownish grey (2-3-9) |
|  | SP | None |
| Potato/carrot extract agar | G | Poor, yellowish grey to dull orange [(1-9-10) to (6-8-6)] |
|  | AM | Normal, powdery, pale yellowish orange (2-9-9) |
|  | R | Pale brown (3-8-6) |
|  | SP | None |

3. Physiological Properties

Tables 5 to 8 show the physiological properties of strains SANK 62285, SANK 62385, SANK 62485 and SANK 62585, respectively. By using Pridham-Gottlieb agar, the assimilation of various carbon sources after cultivation for 14 days was investigated. Since strains SANK 62285, SANK 62385 and SANK 62485 can grow to some degree on control media without a carbon source and SANK 62585 grows well on such control media without a carbon source, it is difficult to assess their exact assimilation capacity. Accordingly, Table 9 shows, for reference, the relative assimilation capacity of these strains on a reference control medium (i.e. an assessment of the *difference* in growth between control media with and without the added carbon source).

TABLE 5

| Properties of Strain SANK 62285 | |
|---|---|
| Hydrolysis of starch | positive |
| Liquefaction of gelatin | positive |
| Reduction of nitrate | negative |
| Coagulation of milk | positive |
| Peptonization of milk | positive |
| Temperature range for growth (Medium 1) | 10–40° C. |
| Optimum temperature for growth (Medium 1) | 20-30° C. |
| Salt resistance (Medium 1) | growth at 7% or below no growth at 10% |
| Melanoid formation | |
| (Medium 2) | negative |
| (Medium 3) | negative |
| (Medium 4) | negative (occasional formation at later stages of culture) |

TABLE 6

| Properties of Strain SANK 62385 | |
|---|---|
| Hydrolysis of starch | positive |
| Liquefaction of gelatin | positive |
| Reduction of nitrate | negative |
| Coagulation of milk | positive |
| Peptonization of milk | positive |
| Temperature range for growth (Medium 1) | 10–40° C. |

TABLE 6-continued

| Properties of Strain SANK 62385 | |
|---|---|
| Optimum temperature for growth (Medium 1) | 26-28° C. |
| Salt resistance (Medium 1) | growth at 7% or below no growth at 10% |
| Melanoid formation | |
| (Medium 2) | negative |
| (Medium 3) | negative |
| (Medium 4) | negative |

TABLE 7

| Properties of Strain SANK 62485 | |
|---|---|
| Hydrolysis of starch | positive |
| Liquefaction of gelatin | positive |
| Reduction of nitrate | negative |
| Coagulation of milk | positive |
| Peptonization of milk | positive |
| Temperature range for growth (Medium 1) | 10–40° C. |
| Optimum temperature for growth (Medium 1) | 20-28° C. |
| Salt resistance (Medium 1) | growth at 7% or below no growth at 10% |
| Melanoid formation | |
| (Medium 2) | negative |
| (Medium 3) | negative |
| (Medium 4) | negative |

TABLE 8

| Properties of Strain SANK 62585 | |
|---|---|
| Hydrolysis of starch | positive |
| Liquefaction of gelatin | negative |
| Reduction of nitrate | positive |
| Coagulation of milk | positive |
| Peptonization of milk | positive |
| Temperature range for growth (Medium 1) | 4–45° C. |
| Optimum temperature for growth (Medium 1) | 15-33° C. |
| Melanoid formation | |
| (Medium 2) | negative |
| (Medium 3) | negative |
| (Medium 4) | doubtful |

In the above Tables 5–8, the media identified as 1–4 are:
Medium 1: Yeast extract Malt extract agar (ISP 2)
Medium 2: Tryptone Yeast extract Broth (ISP 1)
Medium 3: Peptone Yeast extract Iron agar (ISP 6)
Medium 4: Tyrosine agar (ISP 7)

TABLE 9

|  | Strains | | | |
|---|---|---|---|---|
|  | SANK 62285 | SANK 62385 | SANK 62485 | SANK 62585 |
| D-Glucose | + | + | + | + |
| L-Arabinose | − | − | − | − |
| D-Xylose | + | − | ± | + |
| Inositol | − | − | − | + |
| D-Mannitol | − | − | − | − |
| D-Fructose | − | ± | ± | − |
| Sucrose | − | − | − | − |
| Raffinose | − | − | − | + |
| Cellobiose | ND | ND | ND | + |
| Trehalose | ND | ND | ND | + |
| Control | − | − | − | − |

+: Utilized
±: Weakly utilized
−: Not utilized
ND: Not determined

4. Cell Components

The cell walls of strains SANK 62285, SANK 62385, SANK 62485 and SANK 62585 were analyzed by the method of B. Becker et al [Applied Microbiology 12, 421–423 (1964)]. Since L,L-diaminopimelic acid and glycine were identified in the cell walls of all strains, the cell walls were considered to be of type I. The sugar components of the whole cells of the microorganisms were determined by the method of M. P. Lechevalier [Journal of Laboratory and Clinical Medicine 71, 934 (1968)]. No characteristic pattern could be observed.

The results of these taxonomic studies demonstrate that all of the new strains belong to the genus Streptomyces of the actinomycetes and the strains were, accordingly, named Streptomyces sp. SANK 62285, SANK 62385, SANK 62485 and SANK 62585.

The above-mentioned new strains of the genus Streptomyces have been deposited with the Fermentation Research Institute, Ibaraki-ken, Japan as follows: SANK 62285 on Aug. 17, 1985, under the Accession No. FERM P-8419; SANK 62385 on Aug. 17, 1985, under the Accession No. FERM P-8420; SANK 62485 on Aug. 17, 1985, under the Accession No. FERM P-8421; and SANK 62585 on Sep. 5, 1985, under the Accession No. FERM P-8440. All strains were re-deposited on Aug. 13, 1986, under the conditions prescribed by the Budapest Treaty with said Fermentation Research Institute under the Accession Nos. FERM BP-1142, FERM BP-1143, FERM BP-1144 and FERM BP-1145, respectively.

Although the properties of strains SANK 62285, SANK 62385, SANK 62485 and SANK 62585 have been described above, it is well-known that strains of the actinomycetes are unstable in their properties and readily mutate spontaneously or artificially. The present invention envisages both the use of the specific strains identified above, both the Streptomyces strains and the Amycolata strains, as well as mutants of those strains and any other strains of Streptomyces or Amycolata capable of producing an enzyme having the desired hydroxylation effect.

In general, we prefer to employ strains of the species of Streptomyces and Amycolata of which Streptomyces sp. SANK 62285, Streptomyces sp. SANK 62385, Streptomyces sp. SANK 62485, Streptomyces sp. SANK 62585, *Amycolata autotrophica* SANK 62781, *Amycolata autotrophica* subsp. canberrica SANK 62882 and *Amycolata autotrophica* subsp. amethystina SANK 62981 are strains.

The enzymatic hydroxylation process of the present invention can be effected by contacting the ML-236B compound with the chosen microorganism of the genus Amycolats or Streptomyces another method is contacting ML-236B with a cell-free, enzyme-containing extract thereof.

This process of the invention is preferably effected in one of three ways:

(a) adding the starting ML-236B compound to the culture medium during the cultivation of the converting microorganism and then continuing with the cultivation;

(b) collecting cells from a culture of the converting microorganism and contacting the collected cells with the starting ML-236B compound; or (c) preparing a cell-free, enzyme-containing extract from the cells of the converting microorganism and contacting this extract with the starting ML-236B compound.

The converting microorganism of the genus Streptomyces or Amycolats can be cultivated by conventional means in a conventional culture medium containing nutrients well-known for use with such microorganisms. Thus, as is well-known, such culture media contain sources of assimilable carbon and of assimilable nitrogen and often contain inorganic salts. Examples of sources of assimilable carbon include glucose, sucrose, starch, glycerin, millet jelly, molasses and soybean oil. Examples of sources of assimilable nitrogen include soybean solids (such as soybean meal or soybean flour), wheat germ, meat extracts, peptone, corn steep liquor, dried yeast and ammonium salts, such as ammonium sulfate. If required, inorganic salts, such as sodium chloride, potassium chloride, calcium carbonate and various phosphates, may also be included. Also, if desired, other additives capable of promoting the production of hydroxylation enzymes may be employed in appropriate combinations.

The particular cultivation technique employed is not critical to the invention and any technique commonly used for the cultivation of microorganisms of the actinomycetes may equally be employed with the present invention. In general, of course, the techniques employed will be chosen having regard to industrial efficiency. Thus, liquid culture is generally preferred and the submerged culture method is most convenient from the industrial point of view. Cultivation is preferably carried out under aerobic conditions.

Cultivation may be carried out at any temperature at which the microorganism is viable or the enzyme is effective, the temperatures of viability of the microorganisms being given above and in UK Patent No. 2,111,052 in relation to each of the specific strains identified. In general terms, a temperature within the range from 20° to 37° C. is preferred, a temperature from 26° to 28° C. being more preferred.

Method (a) is carried out by adding the starting ML-236B compound to the culture medium in the course of cultivation. The precise point during the cultivation at which the starting compound is added will vary depending upon the cultivation equipment, composition of the medium, temperature of the culture medium and other factors, but it is preferably at the time when the hydroxylation capacity of the microorganism begins to increase, and this is usually 2 or 3 days after beginning cultivation of the microorganism. The amount of ML-236B compound added is preferably from 0.01 to 5.0% by weight of the medium, more preferably from 0.05 to 0.5% by weight. After addition of the starting ML-236B compound, cultivation is continued, preferably aerobically, and normally at a temperature within the ranges proposed above. Cultivation is normally continued for a period of from 3 to 5 days after addition of the starting ML-236B compound.

In Method (b) cultivation of the microorganism is first carried out under conditions such as to achieve its maximum hydroxylation capacity; this capacity usually reaches a maximum between 4 and 5 days after beginning the cultivation, although this period is variable, depending upon the nature and temperature of the medium, the species of microorganism and other factors. The hydroxylation capacity of the culture can be monitored by taking samples of the culture at suitable intervals, determining the hydroxylation capacity of the samples by contacting them with an ML-236B compound under standard conditions and determining the quantity of hydroxylated ML-236B compound obtained. When this hydroxylation capacity has reached its maximum, cultivation is stopped and the microbial cells are collected. This may be achieved by subjecting the culture to centrifugal separation, filtration or similar known separation methods. The whole cells of the cultivated microorganism thus collected are preferably then washed with a suitable washing liquid, such as physiological saline or an appropriate buffer solution.

Contact of the collected cells of the converting microorganism with the ML-236B compound is preferably effected in an aqueous medium, for example in a phosphate buffer solution at a pH value in the range of from 5 to 9. The reaction temperature is preferably within the range from 20° to 45° C., more preferably from 25° to 30° C. The concentration of the ML-236B compound in the reaction medium is preferably within the range from 0.01 to 5.0% by weight. The time allowed for the reaction is normally from 1 to 5 days, although this may vary, depending upon the concentration of ML-236B compound in the reaction mixture, the reaction temperature, the hydroxylation capacity of the microorganism (which may, of course, vary from species to species and will also, as explained above, depend upon the cultivation time) and other factors.

The cell-free, enzyme-containing extract employed in Method (c) may be obtained by breaking down the whole cells of the microorganism obtained as described in relation to Method (b) by physical or chemical means, for example by grinding or ultrasonic treatment, to provide a disintegrated cellular mass, or by treatment with a surface active agent or an enzyme to disrupt the cell walls and produce a cellular solution. The resulting cell-free extract is then contacted with the starting ML-236B compound under the same conditions as are described above in relation to Method (b).

After completion of the conversion reaction by any of the above methods, the product compound can be directly isolated, separated or purified by conventional means. For example, separation and purification can be effected by filtering the reaction mixture, extracting the resulting filtrate with a water-immiscible organic solvent (such as ethyl acetate), distilling the solvent from the extract, subjecting the resulting crude product to column chromatography (for example on silica gel or alumina) and eluting the column with an appropriate eluent. Where the hydroxylated ML-236B compound produced by the microorganism or enzyme is not the desired form of that compound, then the product of the conversion reaction may be subjected to one or more further reactions, such as hydrolysis, salification, esterification or lactonization by conventional means, as described in more detail hereafter. Such additional reactions may be carried out prior to, after or in the course of the separation and purification stages described above, preferably in the course of these stages.

The hydroxylation enzyme active in the process of the invention has no effect in itself on the carboxy group of the ML-236B compound and hence, other factors being equal, ML-236B lactone would give a monohydroxy or dihydroxy ML-236B lactone, ML-236B carboxylic acid would give a monohydroxy or dihydroxy ML-236B carboxylic acid and a salt or ester of ML-236B carboxylic acid would give the same salt or ester of the monohydroxy or dihydroxy ML-236B carboxylic acid. However, this may be affected by other factors, especially the pH value of the reaction mixture, in a way which is predictable by ordinary laws of Chemistry. The ML-236B starting compound and/or monohydroxy or dihydroxy ML-236B compound of the invention may be the free carboxylic acid of formula (II) or (I), respectively, its corresponding lactone or a salt (e.g. metal, amino acid or amine salt) or ester (particularly alkyl ester) thereof.

Preferred metal salts of the starting compound and the compound of the invention are: salts with alkali metals, such as sodium or potassium; salts with alkaline earth metals, such as calcium or magnesium; and salts with other metals, such as aluminum, iron, zinc, copper, nickel or cobalt. Of these, the alkali metal, alkaline earth metal and aluminum salts are preferred, the sodium, potassium, calcium and aluminum salts being most preferred.

Preferred amino acids to form amino acid salts are such basic amino acids as arginine, lysine, histidine, $\alpha,\gamma$-diaminobutyric acid and ornithine.

Preferred amines to form amine salts include t-octylamine, dibenzylamine, dicyclohexylamine, morpholine, alkyl esters of D-phenylglycine and D-glucosamine.

Preferred esters of the starting compounds and of the compounds of the invention are the alkyl esters, particularly $C_1$–$C_6$ alkyl esters, for example the methyl, ethyl, propyl, isopropyl, butyl, isobutyl and pentyl esters, of which the methyl ester is preferred. However, other esters may be employed if desired.

Of the ML-236B compounds used as starting materials, the alkali metal salts, e.g. the sodium or potassium salts, are particularly preferred, the sodium salt being most preferred, as this gives the best conversion of starting compound into the hydroxylated compounds.

Where the product obtained by the enzymatic hydroxylation process of the present invention is a salt of the carboxylic acid of formula (I), the free carboxylic acid itself can be obtained by adjusting the pH of the filtrate to a value of 4 or less, preferably to a value of from 3 to 4, by the addition of an acid. Any organic acid or mineral acid may be employed, provided that it has no adverse effect upon the desired compound. Examples of the many acids which are suitable include trifluoroacetic acid, acetic acid, hydrochloric acid and sulfuric acid. This carboxylic acid may itself be the desired product or it may be, and preferably is, subjected to subsequent reactions, as described below, optionally after such treatments as extraction, washing and dehydration.

Metal salts of the carboxylic acids of formula (I) may be obtained by contacting a hydroxide, carbonate or similar reactive compound of the chosen metal in an aqueous solvent with the carboxylic acid of formula (I). The aqueous solvent employed is preferably water, or it may be a mixture of water with an organic solvent, preferably an alcohol (such as methanol or ethanol), a ketone (such as acetone), an aliphatic hydrocarbon (such as hexane) or an ester (such as ethyl acetate). We particularly prefer to use a mixture of a hydrophilic organic solvent with water. Such reactions are normally conducted at ambient temperature but they may, if desired, be conducted with heating.

Amine salts of the carboxylic acids of formula (I) may be obtained by contacting an amine in an aqueous solvent with the carboxylic acid of formula (I). Suitable aqueous solvents include water and mixtures of water with alcohols (such as methanol or ethanol), ethers (such as tetrahydrofuran), nitriles (such as acetonitrile) or ketones (such as acetone); we particularly prefer to use aqueous acetone as the solvent for this reaction. The reaction is preferably carried out at a pH of from 7 to 8.5 and preferably at a temperature of ambient or below, more preferably a temperature of from 5° to 10° C. The reaction goes immediately to completion. Alternatively, a metal salt of the carboxylic acid of formula (I) (which may have been obtained as described above) can be dissolved in an aqueous solvent (such as those exemplified above), after which a mineral acid salt (for example the hydrochloride) of the desired amine is added, employing the same reaction conditions as when the amine itself is reacted with the carboxylic acid of formula (I), and the desired product is then obtained by a salt exchange reaction.

Amino acid salts of the carboxylic acids of formula (I) may be obtained by contacting an amino acid in an aqueous solvent with the carboxylic acid of formula (I). Suitable aqueous solvents include water and mixtures of water with alcohols (such as methanol or ethanol) or ethers (such as tetrahydrofuran). The reaction is preferably carried out with heating, for example at a temperature of from 50° to 60° C.

Esters, preferably alkyl esters, of the carboxylic acids of formula (I) may be obtained by contacting the carboxylic acid of formula (I) with an appropriate alcohol. We prefer to carry out this reaction in the presence of an acid catalyst, for example a mineral acid (such as hydrochloric acid or sulfuric acid), a Lewis acid (for example boron trifluoride) or an acidic ion exchange resin. The solvent employed for this reaction is not critical, provided that it does not adversely affect the reaction; suitable solvents include benzene, chloroform and ethers (e.g. diethyl ether). Alternatively, the desired product may be obtained by contacting the carboxylic acid of formula (I) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (I) with a halide, preferably an alkyl halide, in a suitable solvent; preferred solvents include dimethylformamide, tetrahydrofuran, dimethyl sulfoxide and acetone. All of the reactions for producing esters are preferably effected at about ambient temperature, although, if required by the nature of the reaction system, the reactions may be conducted with heating.

Lactones of the carboxylic acids of formula (I) may be obtained by contacting the carboxylic acid of formula (I) with a catalytic amount of an acid, which may be organic or inorganic. We prefer to use such organic and mineral acids as trifluoroacetic acid, hydrochloric acid or sulfuric acid. This reaction is preferably effected at about ambient temperature.

The ML-236B derivatives thus obtained can be isolated, separated or purified by conventional means, for example by adsorption on a carrier (such as active carbon or silica gel), or ion exchange chromatography, or gel filtration by a Sephadex (trade mark) column, or by extraction with an organic solvent, such as an ether (e.g. diethyl ether), ethyl acetate or chloroform; if desired, and it is normally preferred, a combination of these techniques may be employed.

If desired, resolution of the isomers can be effected either after completion of the conversion reaction or at any appropriate point during the reactions or during the above-described separation or purification processes.

Specific examples of compounds of the present invention are as follows:
1) 3''-Hydroxy-ML-236B carboxylic acid
2) Sodium 3''-hydroxy-ML-236B carboxylate
3) Potassium 3''-hydroxy-ML-236B carboxylate
4) Calcium 3''-hydroxy-ML-236B carboxylate
5) Aluminum 3''-hydroxy-ML-236B carboxylate
6) Arginine salt of 3''-hydroxy-ML-236B carboxylic acid
7) Lysine salt of 3''-hydroxy-ML-236B carboxylic acid
8) t-Octylamine salt of 3''-hydroxy-ML-236B carboxylic acid
9) Ethyl D-phenylglycinate salt of 3''-hydroxy-ML-236B carboxylic acid
10) Methyl 3''-hydroxy-ML-236B carboxylate
11) 3''-Hydroxy-ML-236B lactone
12) 3'',6'-Dihydroxy-ML-236B carboxylic acid
13) Sodium 3'',6'-dihydroxy-ML-236B carboxylate
14) Potassium 3'',6'-dihydroxy-ML-236B carboxylate
15) Calcium 3'',6'-dihydroxy-ML-236B carboxylate
16) Aluminum 3'',6'-dihydroxy-ML-236B carboxylate
17) Arginine salt of 3'',6'-dihydroxy-ML-236B carboxylic acid
18) Lysine salt of 3'',6'-dihydroxy-ML-236B carboxylic acid
19) t-Octylamine salt of 3'',6'-dihydroxy-ML-236B carboxylic acid
20) Ethyl D-phenylglycinate salt of 3'',6'-dihydroxy-ML-236B carboxylic acid
21) Methyl 3'',6'-dihydroxy-ML-236B carboxylate
22) 3'',6'-Dihydroxy-ML-236B lactone Of the compounds listed above, preferred compounds are Compounds Nos. 1, 2, 11, 12, 13 and 22, the most preferred compounds being the sodium salts, i.e. Compounds No. 2 and 13 of the above list.

The compounds of the invention can exist in the form of various stereoisomers, both geometric isomers due to the positioning of various substituents on the ring systems [as partly shown hereinabove by formulae (Ia), (Ib), (Ic) and (IVa)] and optical isomers due to the presence of asymmetric carbon atoms. Although formula (I) above represents all such isomers in a single formula, the present invention envisages both the individual, isolated isomers and mixtures thereof. Specific isomers or mixtures of isomers may be produced by stereoselective synthesis, but normally mixtures of several isomers are produced and these may, if desired, be used as such, or they may be separated by conventional separation or resolution techniques.

Particularly preferred isomers of the most preferred compounds of the invention are:
23. Sodium 3''α-hydroxy-ML-236B carboxylate
24. Sodium 3''β-hydroxy-ML-236B carboxylate
25. Sodium 3''α,6'β-dihydroxy-ML-236B carboxylate
26. Sodium 3''β,6'β-dihydroxy-ML-236B carboxylate The invention is further illustrated by the following non-limiting Examples.

EXAMPLE 1

3''-Hydroxy-ML-236B lactone

Cells of Streptomyces sp. SANK 62285 (FERM P-8419, BP-1142) were inoculated from a slant culture by means of a platinum loop into each of four 500 ml Erlenmeyer flasks, each containing 100 ml of a culture medium, adjusted to a pH value of 7.0, and containing 20 g per liter glucose, 10 g per liter peptone and 1.0 g per liter yeast extract. Shaking culture was then carried out at 28° C. and 220 rpm on a rotatory shaker for 2 days to give a seed culture.

Each of two 30 liter jar fermentors, each containing 15 liters of a medium having the same composition as defined above, was inoculated with 150 ml of the resulting seed culture and cultivation was continued at 28° C. for 45 hours, whilst aerating at 15 liters per minute and stirring at 100-200 rpm. The internal pressure in the fermentors was 1.0 kg/cm$^2$ and 0.01% w/v of CB-442 antiforming agent was added to each fermentor. At the end of this time, sodium ML-236B carboxylate was added to each fermentor to a final concentration of 1.0% w/v and cultivation was carried out under the same conditions for a further 50 hours. After completion of the cultivation, the culture broth was filtered to give a total of 26 liters of filtrate from the two jar fermentors.

The whole of this filtrate was adsorbed on 2 liters of Diaion HP-20 resin in SV (space velocity) from 4 to 5 liters/hour. The resin was then washed with 8 liters of water and eluted first with 3 liters of 30% v/v aqueous acetone and then with 8 liters of 50% v/v aqueous acetone.

Those fractions (8 liters) eluted with 50% v/v aqueous acetone were concentrated and the acetone stripped off by evaporation under reduced pressure to give 4.6 liters of a concentrate. The pH value of this concentrate was adjusted to 2.8-3.0 by the addition of 6N hydrochloric acid, and then the concentrate was extracted twice, each time with 4 liters of ethyl acetate. The extracts were combined and washed twice, each time with 4 liters of a saturated aqueous solution of sodium chloride. The resulting solution was then dried over anhydrous sodium sulfate and concentrated by evaporation under reduced pressure, to give 20 g of an oily residue. The whole of this oily residue was dissolved in 100 ml of dry ethyl acetate, and 0.5 ml of trifluoroacetic acid was added to the resulting solution. The mixture was then warmed at 50° C. for 3 hours to cause lactonization. At the end of this time, the reaction mixture was diluted with 400 ml of ethyl acetate, washed with a 1% w/v aqueous solution of sodium bicarbonate followed by a saturated aqueous solution of sodium chloride, and then dried over anhydrous sodium sulfate. The resulting ethyl acetate solution was concentrated by evaporation under reduced pressure to a volume of 100 ml and this caused the precipitation as crystals of 12.8 g of crude 3"-hydroxy-ML-236B lactone. A portion of these crystals was purified by chromatography through a silica gel column (Si-60), subjected to gradient elution with hexane to which acetone was progressively added in amounts ranging from 0 to 50% by volume. Pure 3"-hydroxy-ML-236B lactone was obtained from the eluent and had the following physical properties:

1) Molecular formula: $C_{23}H_{34}O_6$
2) Molecular weight: 406 (SIMS spectrum: QM+H, 407)
3) Infrared absorption spectrum: $\nu_{max}$cm$^{-1}$
SIMS is Secondary Ionization Mass Spectroscopy. QM means an Ion Molecule.

Figure 1:
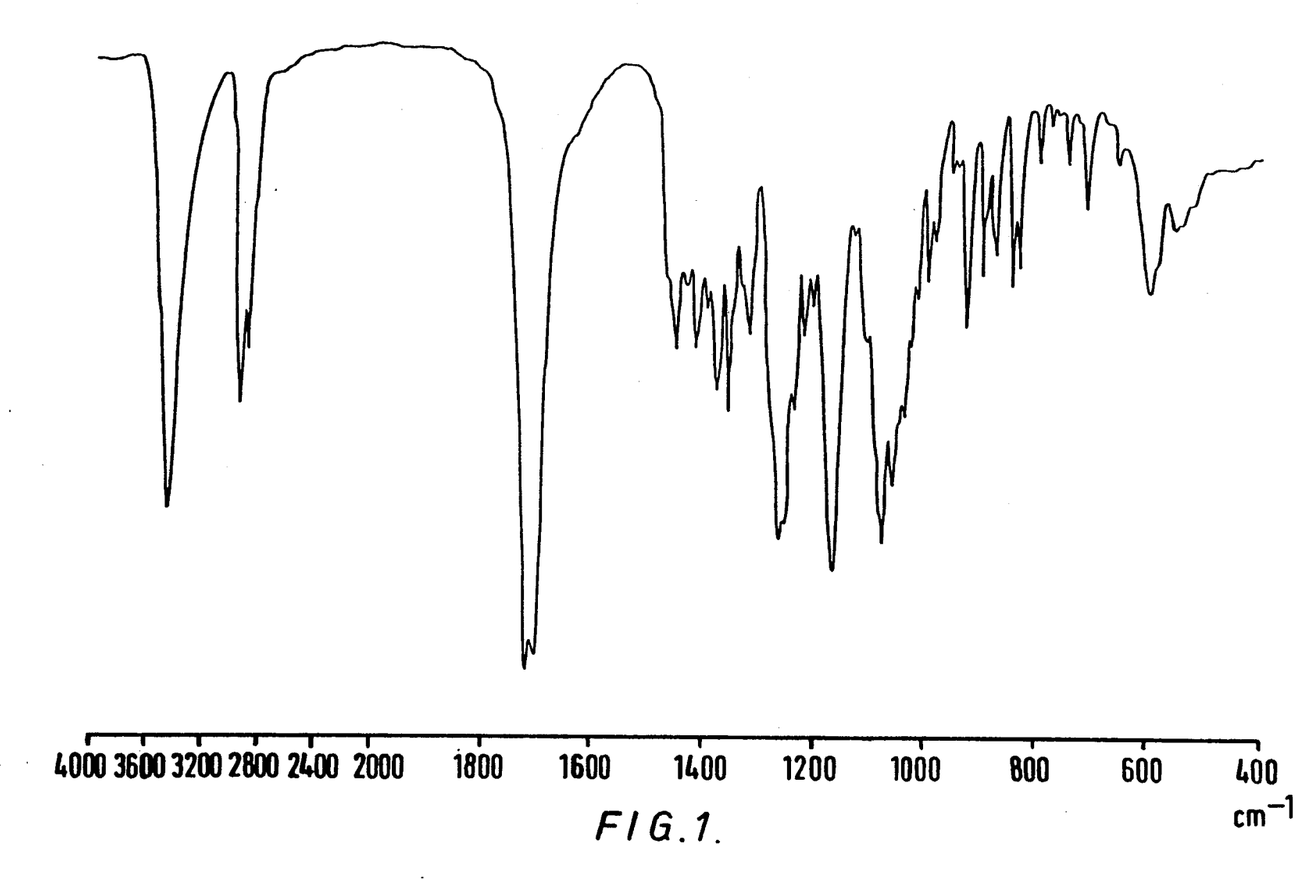
FIG. 1 is an infrared absorption spectrum for 3"-hydroxy-ML-236B lactone.

The infrared absorption spectrum measured as a KBr pellet is shown in FIG. 1 of the accompanying drawings.

4) $^{13}$C Nuclear magnetic resonance spectrum: δppm

The $^{13}$C nuclear magnetic resonance spectrum (22.5 MHz) measured in deuterated chloroform in the presence of tetramethylsilane as an internal standard showed the following chemical shifts (ppm) and multiplicities.

| | chemical shift | multiplicity |
|---|---|---|
| 1 | 10.9 | Quartet |
| 2 | 13.8 | Quartet |
| 3 | 20.0 | Quartet |
| 4 | 20.9 | Triplet |
| 5 | 23.6 | Triplet |
| 6 | 26.2 | Triplet |
| 7 | 30.9 | Doublet |
| 8 | 32.7 | Triplet |
| 9 | 36.9 | Doublet |
| 10 | 36.0 | Triplet |
| 11 | 37.6 | Doublet |
| 12 | 38.6 | Triplet |
| 13 | 45.9 | Doublet |
| 14 | 62.5 | Doublet |
| 15 | 68.1 | Doublet |
| 16 | 68.4 | Doublet |
| 17 | 76.2 | Doublet |
| 18 | 123.6 | Doublet |
| 19 | 128.1 | Doublet |
| 20 | 132.8 | Doublet |
| 21 | 133.7 | Singlet |
| 22 | 170.8 | Singlet |
| 23 | 175.7 | Singlet |

EXAMPLE 2

Sodium 3"-hydroxy-ML-236B carboxylates 2.0 g of 3"-hydroxy-ML-236B lactone, prepared as described in Example 1, were dissolved in 200 ml of methanol, and the solution was diluted with 50 ml of distilled water. About a molar equivalent of aqueous sodium hydroxide (0.25 g in 40 ml of water) was added dropwise to the solution at 40°-50° C. In the course of the addition, the production of the sodium salt was confirmed by liquid chromatography. Two hours after the addition, the reaction mixture was adjusted to a pH value of 8.5 by addition of 1N hydrochloric acid, and the methanol was evaporated off under reduced pressure to reduce the volume to 50 ml. The aqueous residue was lyophilized to give 2.6 g of sodium 3"-hydroxy-ML-236B carboxylate, which had the following physical constants.

Figure 2:
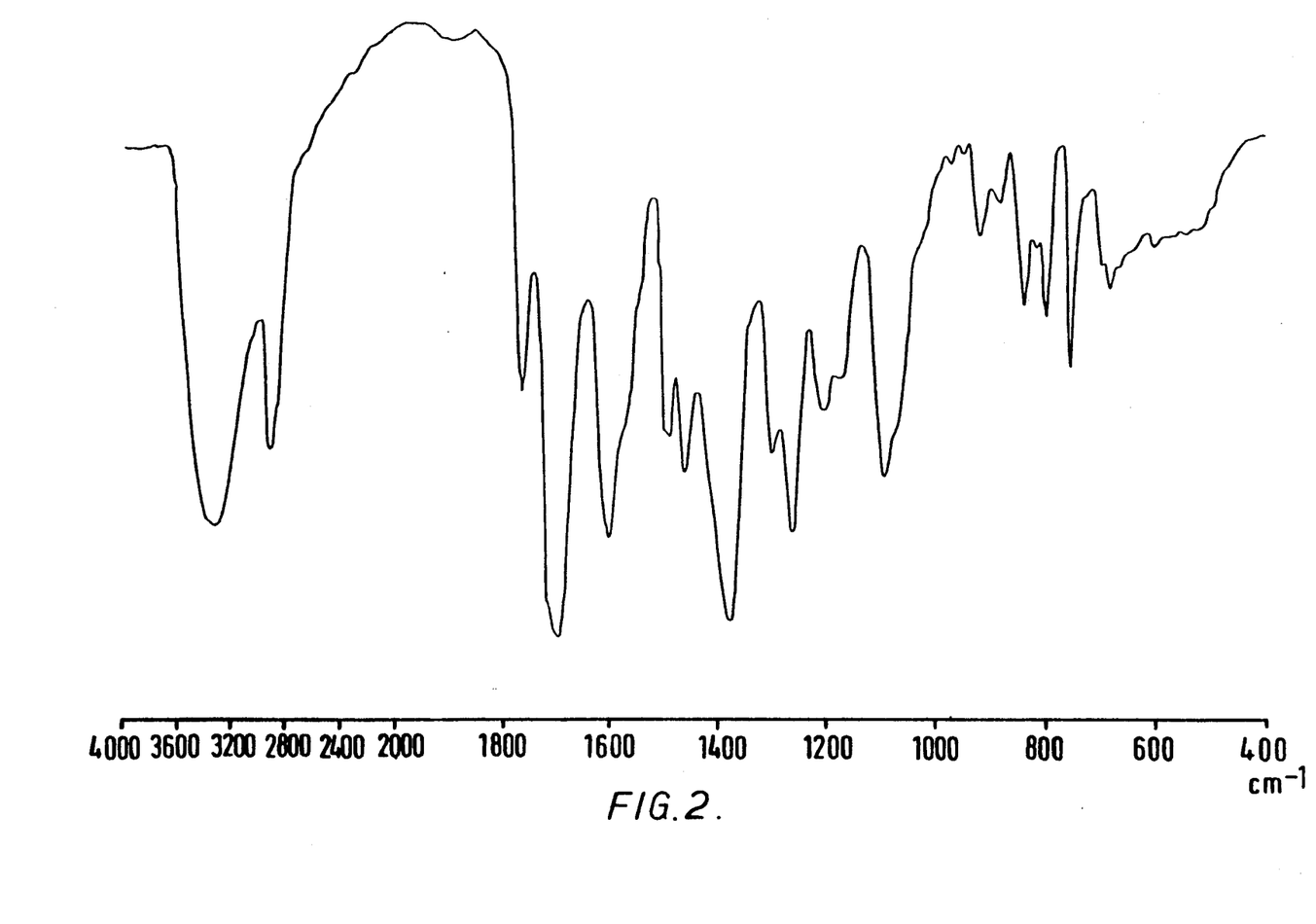
FIG. 2 is an infrared absorption spectrum for sodium 3"-hydroxy-ML-236B carboxylate.

1) Molecular formula: $C_{23}H_{35}O_7Na$
2) Infrared absorption spectrum: $\nu_{max}$cm$^{-1}$ The infrared absorption spectrum measured as a KBr pellet is shown in FIG. 2.

Figure 3:
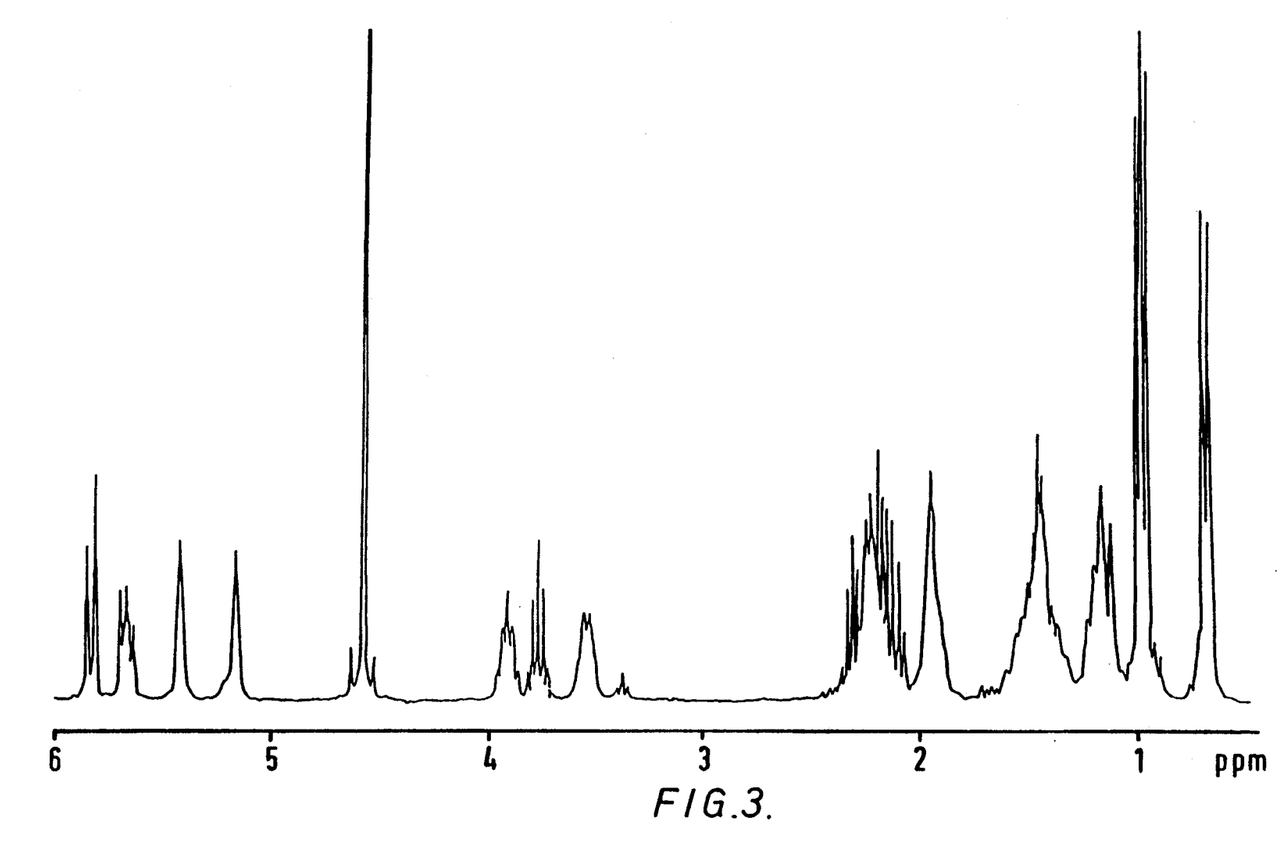
FIG. 3 is a proton resonance spectrum for sodium 3"-hydroxy-ML-236B carboxylate.

Proton nuclear magnetic resonance spectrum (270 MHz) measured in heavy water in the presence of tetramethyl silane as an internal standard is shown in FIG. 3.
3) $^{13}$C nuclear magnetic resonance spectrum: δ ppm The $^{13}$C nuclear magnetic resonance spectrum (22.5 MHz) measured in deuterium oxide in the presence of 1,4-dioxane as an internal standard showed the following chemical shifts (ppm) and multiplicities.

| | chemical | multiplicity |
|---|---|---|
| 1 | 13.8 | Quartet |
| 2 | 14.7 | Quartet |
| 3 | 21.7 | Quartet |
| 4 | 21.9 | Doublet |
| 5 | 25.2 | Triplet |
| 6 | 27.0 | Doublet |
| 7 | 31.8 | Doublet |
| 8 | 35.5 | Triplet |
| 9 | 38.2 | Triplet |
| 10 | 38.3 | Triplet |
| 11 | 44.6 | Triplet |
| 12 | 45.6 | Triplet |

-continued

| | chemical | multiplicity |
|---|---|---|
| 13 | 48.6 | Doublet |
| 14 | 68.8 | Doublet |
| 15 | 69.4 | Doublet |
| 16 | 70.0 | Doublet |
| 17 | 71.1 | Doublet |
| 18 | 124.0 | Doublet |
| 19 | 129.0 | Doublet |
| 20 | 134.5 | Doublet |
| 21 | 135.0 | Singlet |
| 22 | 177.7 | Singlet |
| 23 | 180.9 | Singlet |

EXAMPLE 3

The procedure described in Examples 1 and 2 was repeated, but using Streptomyces sp. SANK 62385 (FERM P-8420, BP-1143) or Streptomyces sp. SANK 62485 (FERM P-8421, BP-1144) in place of Streptomyces sp. SANK 62285, to give 3″-hydroxy-ML-236B lactone and sodium 3″-hydroxy-ML-236B carboxylate, respectively, whose physical properties were the same as those of the products of Examples 1 and 2.

EXAMPLE 4

Sodium 3″α,6′β-dihydroxy-ML-236B carboxylate and sodium 3″β,6′β-dihydroxy-ML-236B carboxylate Cells of *Amycolata autotrophica* subsp. amethystina SANK 62981 (FERM P-6183) were inoculated from a slant culture by means of a platinum loop into each of twenty 500 ml Erlenmeyer flasks, each containing 100 ml of a culture medium having the following composition (percentages are w/v):

| Glucose | 1.0% |
|---|---|
| Peptone | 0.2% |
| Meat extract | 0.1% |
| Yeast extract | 0.1% |
| Corn steep liquor | 0.3% |
| Tap water | balance (pH not adjusted) |

Shaking culture was then carried out at 30° C. and 220 r.p.m. on a rotatory shaker for 2 days, at which time sodium ML-236B carboxylate was added to a final concentration of 0.05% w/v. Incubation was continued at 26° C. and 220 r.p.m. for a further 5 days.

After completion of the cultivation, the cultured broth was filtered, and the filtrate was adjusted to a pH value of 8.5 by the addition of sodium hydroxide. It was then absorbed on a column containing 600 ml of highly porous Diaion (trade mark) HP-20 polymer. The column was then washed with 3,600 ml of water and then eluted with 1,200 ml of water containing 20% by volume of methanol. The eluent was concentrated by evaporation under reduced pressure and then lyophilized to give 610 mg of a solid material. This material was separated into two substances, which we call "Substance A" and "Substance B", by liquid chromatography through an SSC-ODS-2942 column of diameter 30 mm and length 250 mm. Elution using water containing 30% by volume of methanol initially gave Substance A, and this was followed by Substance B. The eluents were separately concentrated by evaporation under reduced pressure, and then lyophilized, to give 50 mg of Substance A and 55 mg of Substance B.

Substances A and B are configurational isomers of the hydroxy group at the 3″ position; in one of them, the hydroxy group has the α-orientation whilst, in the other, it has the β-orientation, but it is not presently known which is which.

Physical properties of Substances A and B are as follows:

1) Molecular formula: $C_{23}H_{35}O_8Na$

2) Molecular weight: FAB-MS of both Substances A and B shows m/z 463 $(M+H)^+$ and 485 $(M+NA)^+$. FAB-MS is Fast Atom Bombardment Mass Spectroscopy.

Figure 4:
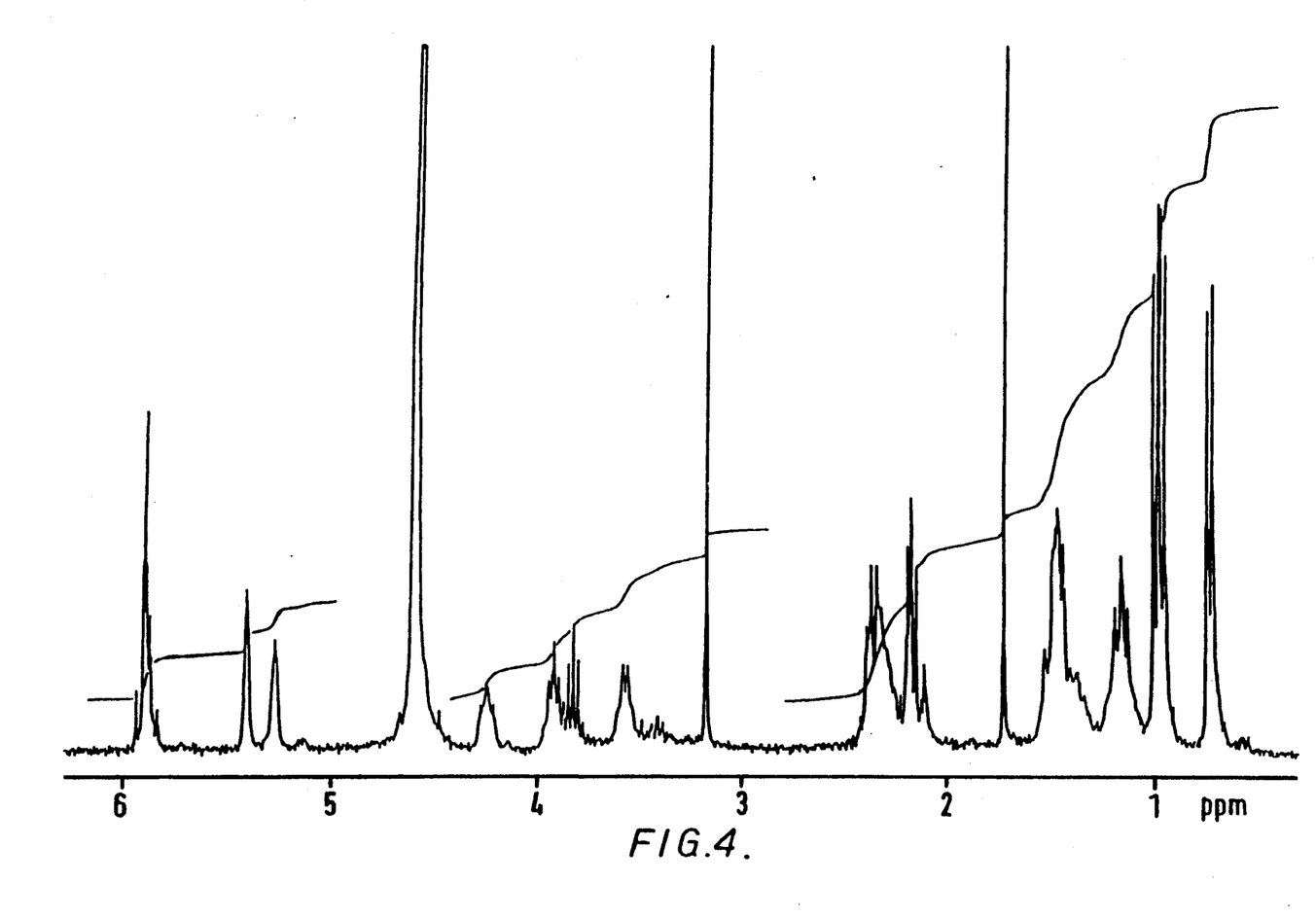
FIG. 4 is a nuclear magnetic resonance spectrum for sodium 3"α, 6'β-dihydroxy-ML-236B carboxylate.
Figure 5:
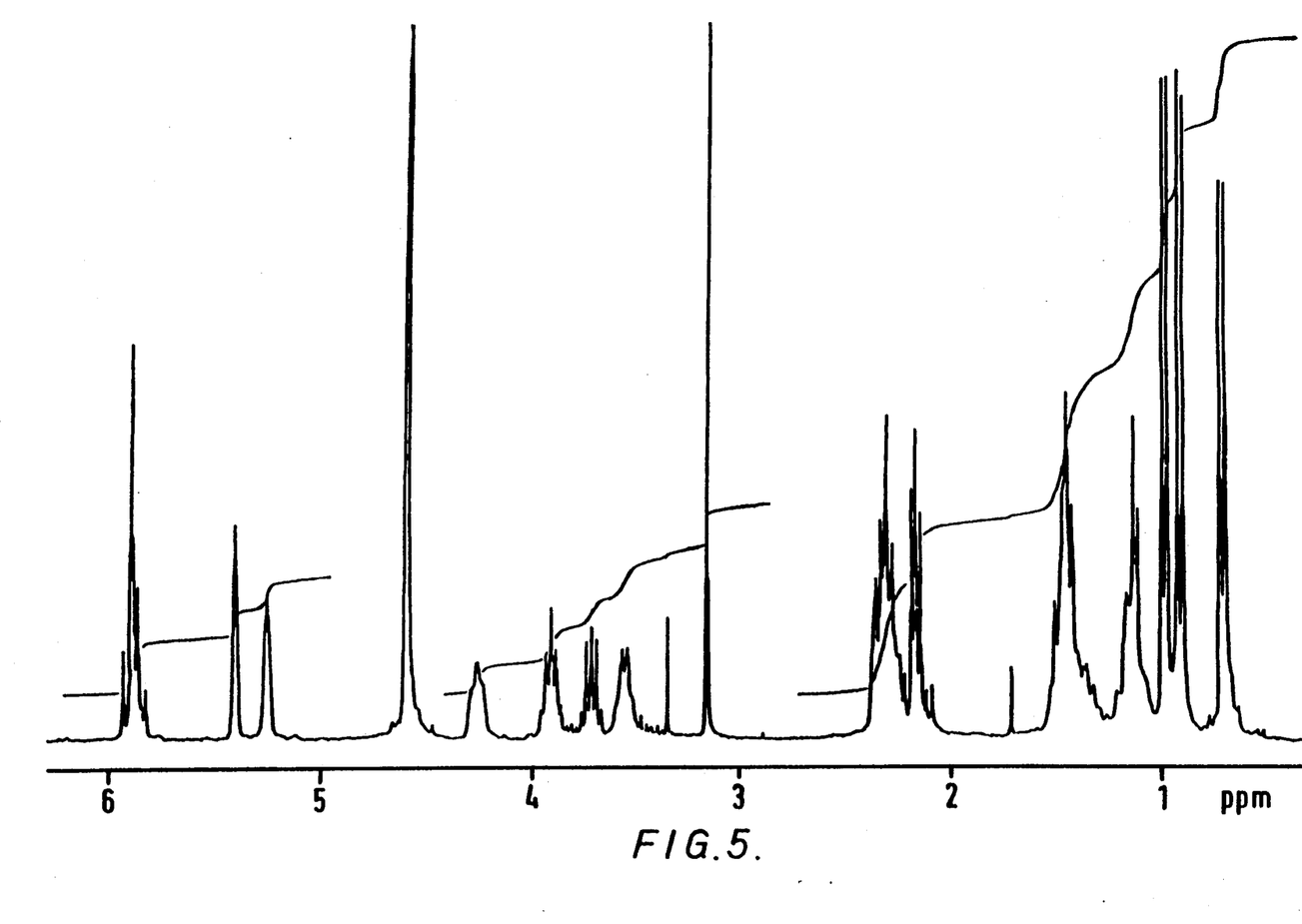
FIG. 5 is a nuclear magnetic resonance spectrum for sodium 3"β, 6'β-dihydroxy-ML-236B carboxylate.

3) Nuclear magnetic resonance spectra (270 MHz) measured in deuterium oxide in the presence of tetramethylsilane as an internal standard are shown FIG. 4 (Substance A) and FIG. 5 (Substance B).

4) High speed liquid chromatography: Substances A and B have retention times of 4.833 minutes and 5.5 minutes, respectively, under the following conditions: column, inside diameter about 6 mm, length about 10 cm, ERC-ODS-1262 (ERMA Co., Ltd.); mobile phase methanol: water:acetic acid:triethylamine (500:500:1:1 by volume); column temperature 40° C.; flow rate 1.0 ml/minute; detector ultraviolet 238 nm.

5) Gas chromatography: Substances A and B show retention times of 25.475 minutes and 24.563 minutes, respectively, under the following conditions: column inside diameter about 0.2 mm, length about 25 meters, chemically bonding type methylsilicone membrane of 0.33 μm thickness (Hewlett Packard Co., Ltd., ULTRA#1); column temperature about 280° C.; temperature of evaporation chamber and detector about 300° C.; carrier gas helium 2.0 ml/minute; detector hydrogen flame ionization detector.

EXAMPLE 5

Sodium 3″α,6′β-dihydroxy-ML-236B carboxylate and sodium 3″β,6′β-dihydroxy-ML-236B carboxylate Cells of Streptomyces sp. SANK 62585 (FERM P-8440, BP-1145) were inoculated from a slant culture by means of a platinum loop into each of twenty 500 ml Erlenmeyer flasks, each containing 100 ml of a culture medium having the following composition (percentages are w/v):

| Glucose | 2.0% |
|---|---|
| Peptone | 1.0% |
| Yeast extract | 0.1% |
| Tap water (pH 7.0). | balance |

Shaking culture was then carried out at 27°-28° C. and 220 rpm for 2 days. At the end of this time, sodium ML-236B carboxylate was added to a final concentration of 0.05% w/v. Incubation was continued at 27°-28° C. and 220 rpm for a further 5 days.

At the end of this time, the cultured broth was filtered, and the filtrate was adjusted to a pH value of 8.5 by the addition of sodium hydroxide. The resulting solution was then adsorbed on a column containing 600 ml of Diaion HP-20, a highly porous polymer. The column was then washed with 3,600 ml of water and eluted with 1,200 ml of water containing 20% by volume of methanol.

The eluent was concentrated by evaporation under reduced pressure and then lyophilized, to give 720 mg of a solid material. This material was purified by liquid chromatography using an SSC-ODS-2942 column of 30 mm diameter and 250 mm long. Elution with water containing 30% by volume of methanol gave Substance A first, followed by Substance B. Each of the eluents was separately concentrated by evaporation under reduced pressure, and then lyophilized, to give 45 mg of Substance A and 38 mg of Substance B. The physical constants of these Substances were identical with those of the respective Substances produced in Example 4.

BIOLOGICAL ACTIVITY

Inhibitory Activity Against Cholesterol Biosynthesis

The inhibitory activities of certain of the compounds of the invention, in terms of the concentration in μg/ml required to inhibit cholesterol biosynthesis by 50% [measured by the method described in the Journal of Biological Chemistry, 234, 2835 (1959)], are as follows:

| | |
|---|---|
| 3″-hydroxy-ML-236B lactone | 0.039 |
| Sodium 3″-hydroxy-ML-236B carboxylate | 0.0032 |
| Sodium 3″,6′β-dihydroxy-ML-236B carboxylate, Substance A | 0.0018 |
| Sodium 3″,6′β-dihydroxy-ML-236B carboxylate, Substance B | 0.024 |
| ML-236B lactone (for comparison) | 0.010 |

From the above results, it can be seen that the compounds of the invention have activities comparable with or significantly better than those of ML-236B lactone in their ability to inhibit 3-hydroxy-3-methylglutaryl-CoA reductase, which acts as the rate-limiting enzyme in cholesterol biosynthesis.

We claim:

1. A process for preparing a compound of formula (I):

wherein R represents a hydrogen atom or a hydroxy group, pharmaceutically acceptable salts and esters thereof and the corresponding ring-closed lactones of the formula which process comprises contacting an ML-236B compound selected from the group consisting of ML-236B carboxylic acid of the formula salts and esters of ML-236B carboxylic acid and ML-236B lactone of the formula with a hydroxylation enzyme produced by a microorganism selected from the group consisting of microorganisms of the genus Streptomyces and microorganisms of the genus Amycolata; if necessary, subjecting the resulting product to one or more reactions selected from the group consisting of hydrolysis, salification, esterification and lactonization; and isolating the product from the reaction mixture.

2. The process as claimed in claim 1, wherein the compound isolated is a compound in which R represents a hydrogen atom.

3. The process as claimed in claim 2, wherein said microorganism of the genus Streptomyces is a microorganism of a species of which Streptomyces sp. SANK 62285 is a strain.

4. The process as claimed in claim 2, wherein said microorganism of the genus Streptomyces is a microorganism of a species of which Streptomyces sp. SANK 62385 is a strain.

5. The process as claimed in claim 2, wherein said microorganism of the genus Streptomyces is a microorganism of a species of which Streptomyces sp. SANK 62485 is a strain.

6. The process as claimed in claim 2, wherein said microorganism is selected from the group consisting of Streptomyces sp. SANK 62285, Streptomyces sp. SANK 62385 and Streptomyces sp. SANK 62485.

7. The process as claimed in claim 1, wherein R represents a hydroxy group.

8. The process as claimed in claim 7, wherein said microorganism of the genus Amycolata is a microorganism of a species of Amycolata of which *Amycolata autotrophica* SANK 62781 is a strain.

9. The process as claimed in claim 7, wherein said microorganism of the genus Amycolata is a microorganism of a species of Amycolata of which *Amycolata autotrophica* subsp. canberrica SANK 62882 is a strain.

10. The process as claimed in claim 7, wherein said microorganism of the genus Amycolata is a microorganism of a species of Amycolata of which *Amycolata autotrophica* subsp. amethystina SANK 62981 is a strain.

11. The process as claimed in claim 7, wherein said microorganism of the genus Amycolata is a microorganism selected from the group consisting of *Amycolata autotrophica* SANK 62781, *Amycolata autotrophica* subsp. canberrica SANK 62882 and *Amycolata autotrophica* subsp. amethystina SANK 62981.

12. The process as claimed in claim 7, wherein said microorganism of the genus Streptomyces is a microorganism of a species of which Streptomyces sp. SANK 62585 is a strain.

13. The process as claimed in claim 7, wherein said microorganism of the genus Streptomyces is Streptomyces sp. SANK 62585.

14. A microorganism of the genus Streptomyces selected from the group consisting of Streptomyces having the accession Numbers FERM BP-1142; FERM BP-1143; FERM BP-1144; and FERM BP-1145.

15. A culture comprising the microorganism of claim 14, said culture being capable of producing an hydroxylation enzyme in recoverable quantities, when cultured, which will convert ML236B of the formula in its lactone form into a compound of the formula (I):

wherein R represents a hydrogen atom or a hydroxy group; said compound including the pharmaceutically acceptable salts and esters thereof formed at the carboxy group, or the corresponding ring-closed lactones having the formula (Id):

16. The microorganism of the genus Streptomyces as claimed in claim 14, wherein the microorganism has the accession number FERM BP-1145.

* * * * *